United States Patent
Zhang

(10) Patent No.: US 7,339,077 B2
(45) Date of Patent: Mar. 4, 2008

(54) PRODUCTION PROCESS OF DICREATINE MALATE

(76) Inventor: Guoji Zhang, 16 Xinhua Rd., Yangliuqing, Tianjin (CN)

(*) Notice: Subject to any disclaimer, the term of this patent is extended or adjusted under 35 U.S.C. 154(b) by 186 days.

(21) Appl. No.: 10/842,800

(22) Filed: May 10, 2004

(65) Prior Publication Data

US 2005/0250962 A1    Nov. 10, 2005

(51) Int. Cl.
*C07C 241/00* (2006.01)
(52) U.S. Cl. .................................................. 562/560
(58) Field of Classification Search .............. 562/560
See application file for complete search history.

(56) References Cited

U.S. PATENT DOCUMENTS

2004/0133040 A1* 7/2004 Boldt ..................... 562/560

OTHER PUBLICATIONS

Hawley, The Condesed Chemical Dictionary, 1971, Van Nostand Reinhold Com., 8th ed. p. 780,(3 pages).*

* cited by examiner

*Primary Examiner*—Taylor Victor Oh
(74) *Attorney, Agent, or Firm*—Raymond Y. Chan; Davis and Raymond Patent Group

(57) ABSTRACT

A process of producing dicreatine malate with high purity, includes the steps of providing a predetermined amount of malic acid, agitating a predetermined amount of anhydrous alcohol to the malic acid to obtain a first solution, filtering the first solution to form a clear solution, agitating a predetermined amount of creatine to the clear solution to obtain a second solution, centrifuging the second solution to obtain a wet dicreatine malate and a separated alcohol, and drying the wet dicreatine malate to produce a dicreatine. Because of its low energy consumption, this process produces dicreatine malate effectively.

10 Claims, 2 Drawing Sheets

PRODUCTION PROCESS OF DICREATINE MALATE

BACKGROUND OF THE PRESENT INVENTION

1. Field of Invention

The present invention relates to a production process of dicreatine malate, comprising the steps of providing a predetermined amount malic acid, dissolving the malic acid with a predetermined amount of an anhydrous alcohol to form a first solution, filtering the first solution to form a clear solution, agitating a predetermined amount of creatine to the clear solution to form a second solution, centrifuging the second solution to form a wet dicreatine malate, and drying the wet dicreatine malate to yield a dicreatine malate of a purity of at least 98%, such that dicreatine malate can easily be mass produced under a simple and cost effective process.

2. Description of Related Arts

Dicreatine malate is a highly soluble creatine salt, which provides creatine for muscle growth in a body. Creatine increases muscle volume by increasing the muscle's ability to uphold fluid. As a result, muscle will increase in weight, size, as well as strength.

Creatine is essentially an amino acid derivative which can be naturally found in animal muscle tissue, enabling muscles to produce in a high rate high-energy compounds (ATP). Creatine is created by the human liver and kidneys, by the breaking down of amino acids. Due to its chemical property, supplements of creatine have been taken for muscle cells to store energy for sprinting and explosive exercise.

Before dicreatine malate was created, people who wish to build their body originally would obtain an essential amount of creatine from the regular creatine. However, it was eventually found that regular creatine has many side effects such as causing stomach upset, and causing the body to hold subcutaneous water due to the water molecule in its chemical structure. Creatine was also found to be not readily soluble, which causes intaking uneasy.

Since dicreatine malate was found to cause no side effect, and, most importantly, requires no loading when taken as a supplement for body-building, it is now widely accepted for replacing creatine. Dicreatine malate is also 4-7 times more readily soluble when comparing with creatine itself.

Dicreatine malate is therefore now in high demand thus various process has been developed for that purpose. U.S. Pat. No. 5,973,199 (199') disclosed a hydrosoluble organic salts of creatine, including a process of producing the same. That process involves a lot of energy and time consuming steps including concentrating, cooling and drying under vacuum, and yet, the dicreatine salt yield is only 87%.

As a result, a new process has to be developed to produce more economical, less energy consuming and higher purity dicreatine malate.

SUMMARY OF THE PRESENT INVENTION

A main object of the present invention is to provide a simple and cost effective producing process of dicreatine malate.

Another object of the present invention is to provide a process of producing dicreatine malate, wherein the steps are simple and easy to carry out, which requires low energy consumption.

Another object of the present invention is to provide a process of producing dicreatine malate, wherein the reactants are readily available and easy to obtain.

Another object of the present invention is to provide a process of producing dicreatine malate, wherein the final product has a creatine malate content of greater than 98%.

Another object of the present invention is to provide a process of producing dicreatine malate, wherein the separated alcohol is recycled for dissolving the malic acid, such that the production cost of dicreatine malate is decreased.

Accordingly, in order to accomplish the above objects, the present invention provides a production process of dicreatine malate, comprising the steps of:

(a) providing a predetermined amount of malic acid;

(b) dissolving the malic acid with a predetermined amount of anhydrous alcohol to obtain a first solution;

(c) filtering the first solution to form a clear solution;

(d) agitating a predetermined amount of creatine to the clear solution to obtain a second solution;

(e) centrifuging the second solution to obtain a wet dicreatine malate and a recycled alcohol; and (f) drying the wet dicreatine malate to yield a dicreatine malate having a purity of at least 98%.

These and other objectives, features, and advantages of the present invention will become apparent from the following detailed description, the accompanying drawings, and the appended claims.

DETAILED DESCRIPTION OF THE PREFERRED EMBODIMENT

Figure 1:
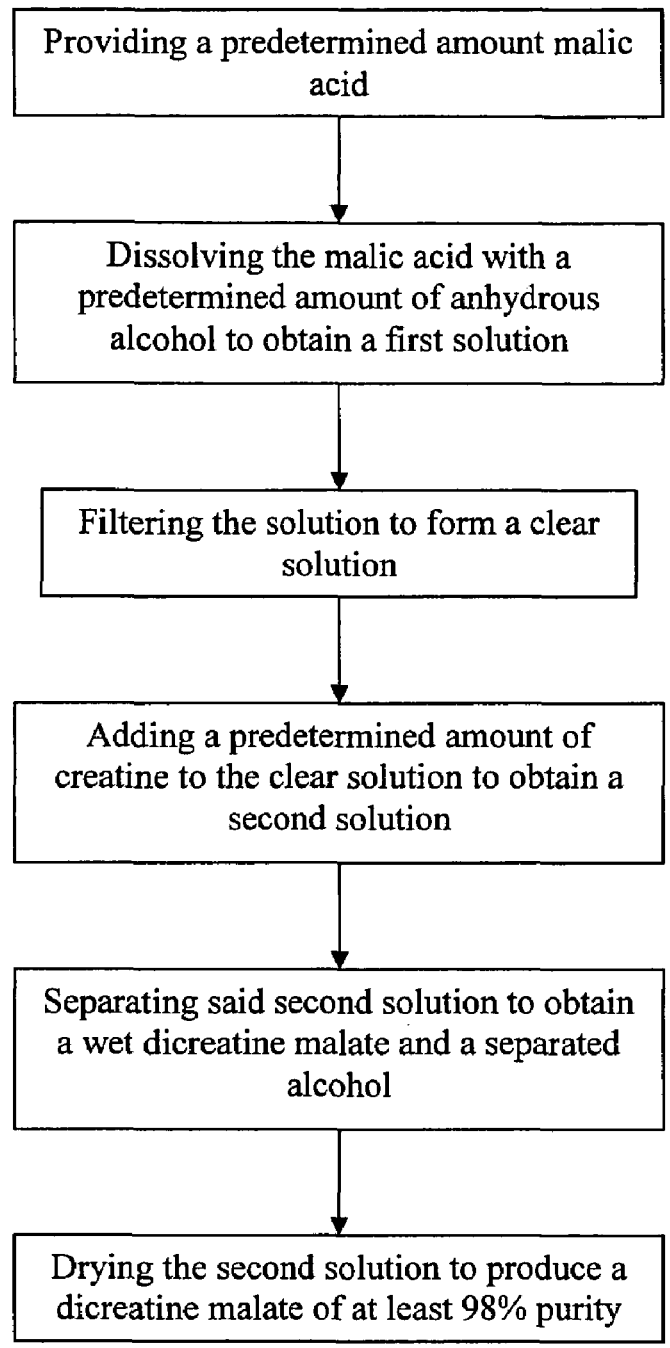
FIG. 1 is a flow chart illustrating a process of producing dicreatine malate according to a preferred embodiment of the present invention.

Referring to FIG. 1 of the drawings, a process of producing dicreatine malate according to a preferred embodiment of the present invention is illustrated, wherein the process comprises the steps of (a) providing a predetermined amount of malic acid, (b) dissolving the malic acid with an anhydrous alcohol to obtain a first solution, (c) filtering the first solution to obtain a clear solution, (d) agitating a predetermined amount of creatine to the clear solution to obtain a second solution, (e) centrifuging the second solution to form a wet dicreatine malate, and (f) drying the wet dicreatine malate to produce a dicreatine malate having a purity of at least 98%.

The chemical equation of the production of dicreatine malate by reacting malic acid and creatine is:

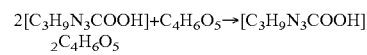

$$2[C_3H_9N_3COOH] + C_4H_6O_5 \rightarrow [C_3H_9N_3COOH]_2 C_4H_6O_5$$

According to the preferred embodiment, in the step (a), the malic acid is a concentrated malic acid. The preferred concentration of the malic acid is 99% by volume. The malic acid is in solid form. In order to dissolve the malic acid, an anhydrous alcohol is added as a solvent to dissolve the malic acid to obtain a first solution. In order to provide a well mixed solution, it is preferred to provide agitation to the solution.

In the step (b), the anhydrous alcohol acts as a solvent, so that it does not react with the malic acid. In fact, after the reaction between the solution and the creatine, the alcohol is separated out from the product through a separation process.

It is worth mentioning that the anhydrous alcohol to be used in the preferred embodiment is anhydrous ethanol.

According to the preferred embodiment, the amount of malic acid and anhydrous ethanol are 25.2 kg and 50.4-100.8 kg respectively. Furthermore, the agitation is preferred to be carried out at a temperature of between 65° C. to 70° C.

In the step (c), in order to provide a clear solution for the reaction between the creatine and the solution, the solution is filtered so as to take away any undissolved malic acid or other residual and to form the clear solution.

In the step (d), a predetermined amount of creatine is then added to the clear solution so as to react to obtain a second solution. Again, in order to have a better reaction between the creatine and the clear solution, it is preferred to provide agitation to the reactants.

According to this preferred embodiment of the present invention, a 60 kg of creatine is added to the clear solution.

Preferably, but not limited to, the creatine is added to the clear solution at 75° C. and the reactants are then agitated at a temperature below 75° C. for 30 minutes.

Since the second solution contains dicreatine malate and the ethanol, in order to obtain the dicreatine malate, the ethanol and the dicreatine malate in the second solution has to be separated by undergoing a separation process.

According to the preferred embodiment of the present invention, in the step (e), the ethanol and the dicreatine malate is separated by a centrifugal force, wherein the centrifugal force is provided by a centrifuge. The second solution is preferred to be separated by the centrifuge at a temperature below 25° C.

The separation process produces a wet dicreatine malate and a separated ethanol. Finally, in order to obtain the targeted above 98% purity dicreatine malate, the wet dicreatine malate undergoes the step (f) drying, in which the wet dicreatine malate is dried at a drying temperature of between 50° C. and 60° C. A dicreatine malate having a purity of 98% is produced.

Figure 2:
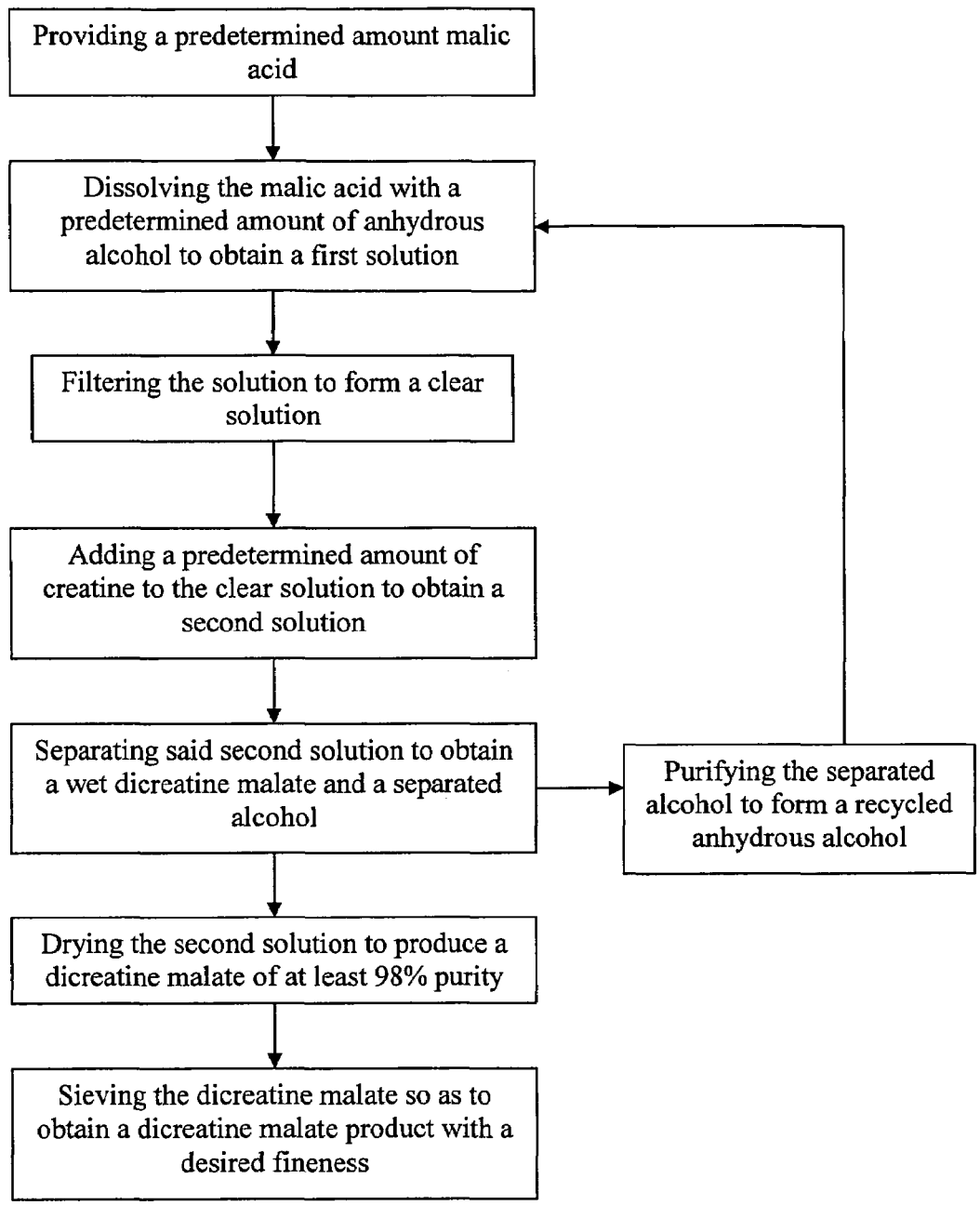
FIG. 2 is a flow chart illustrating the full process of producing dicreatine malate according to the above preferred embodiment of the present invention.

According to FIG. 2 of the drawings, since there is the separated ethanol produced after the separation process, the process of the present invention further comprises a step of purifying the separated ethanol to form a recycled anhydrous ethanol, such that it is recycled for dissolving the malic acid. By doing so, the production cost of dicreatine malate is reduced.

Furthermore, after the completion of the production process, in order to provide a dicreatine malate of a desirable fineness to the consumers, the production process of dicreatine malate further comprises a step of sieving the dicreatine malate, so as to obtain a dicreatine malate powder of a predetermined fineness.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A process of producing dicreatine malate, comprising the steps of:
    (a) dissolving a malic acid with an anhydrous ethanol, in a ratio between 25.2:50.4 and 20.5:100.8 and at a temperature between 65° C. and 70° C., to obtain a first solution;
    (b) filtering said first solution to form a clear solution;
    (c) adding a creatine to said clear solution at a temperature below 75° C. to obtain a second solution;
    (d) centrifuging said second solution to obtain a wet dicreatine malate and a separated alcohol at a temperature below 25° C.; and
    (e) drying said wet dicreatine malate at a temperature between 50° C. and 60° C. to produce a dicreatine malate having a purity of at least 98%.

2. The process, as recited in claim 1, wherein said separated alcohol is ethanol.

3. The process, as recited in claim 1, wherein the step (c) is processed for a period of 30 minutes.

4. The process, as recited in claim 1, wherein in the step (c), a 60 kg of creatine is used.

5. The process, as recited in claim 1, wherein said malic acid is in solid form having a concentration of 99% by volume.

6. The process, as recited in claim 4, wherein said malic acid is in solid form having a concentration of 99% by volume.

7. The process, as recited in claim 1, further comprises the steps of:
    (f) purifying said separated alcohol to form a recycled anhydrous alcohol; and
    (g) recycling said recycled anhydrous alcohol for dissolving said malic acid.

8. The process, as recited in claim 6, further comprises the steps of:
    (h) purifying said separated alcohol to form a recycled anhydrous alcohol; and
    (i) recycling said recycled anhydrous alcohol for dissolving said malic acid.

9. The process, as recited in claim 1, further comprising a step of sieving said dicreatine malate to obtain a dicreatine malate product with a desired fineness.

10. The process, as recited in claim 8, further comprising a step of sieving said dicreatine malate to obtain a dicreatine malate product with a desired fineness.

* * * * *